United States Patent [19]
Chang

[11] Patent Number: 5,092,845
[45] Date of Patent: Mar. 3, 1992

[54] CATHETER WITH NEEDLE GASKET

[75] Inventor: Joseph J. Chang, Tampa, Fla.

[73] Assignee: Critikon, Inc., Tampa, Fla.

[21] Appl. No.: 377,381

[22] Filed: Jul. 10, 1989

[51] Int. Cl.$^5$ .............................................. A61M 5/178
[52] U.S. Cl. .................................... 604/164; 604/168
[58] Field of Search ...................... 604/164, 167–169, 604/192, 197, 198, 240, 256, 263, 900

[56] References Cited

U.S. PATENT DOCUMENTS

| 3,559,645 | 2/1971 | Schaller | 128/216 |
| 4,044,765 | 8/1977 | Kline | 128/214.4 |
| 4,248,246 | 2/1981 | Ikeda | 128/765 |
| 4,581,024 | 4/1986 | Swenson | 604/240 |
| 4,832,696 | 5/1989 | Luther et al. | 604/198 |
| 4,834,718 | 5/1989 | McDonald | 604/198 |
| 4,846,809 | 7/1989 | Sims | 604/198 |
| 4,850,374 | 7/1989 | Diaz-Ramos | 604/198 |
| 4,917,679 | 4/1990 | Kronner | 604/198 |

FOREIGN PATENT DOCUMENTS

| 1456725 | 11/1976 | Canada . |
| 0139091 | 5/1985 | European Pat. Off. . |
| 2930617 | 2/1980 | Fed. Rep. of Germany . |
| 8906101.2 | 8/1989 | Fed. Rep. of Germany . |
| 2215976 | 8/1974 | France . |

Primary Examiner—John D. Yasko
Assistant Examiner—Anthony Gutowski
Attorney, Agent, or Firm—Paul A. Coletti

[57] ABSTRACT

A catheter assembly is provided with a needle guard that slides along the needle to shield the distal tip of the needle after the needle is withdrawn from a patient. The needle passes through an aperture at the distal end of the needle guard. To prevent the backflow of blood through the aperture and into the needle guard, a gasket is formed in the aperture about the needle. The gasket is formed with the needle in place by filling the aperture around the needle with adhesive. After the adhesive has substantially cured but before the adhesive has tightly bonded to the needle the needle guard is moved along the needle to prevent bonding of the adhesive to the needle. The needle guard will thereafter slide along the needle with the needle passing through the formed-in-place gasket.

8 Claims, 4 Drawing Sheets

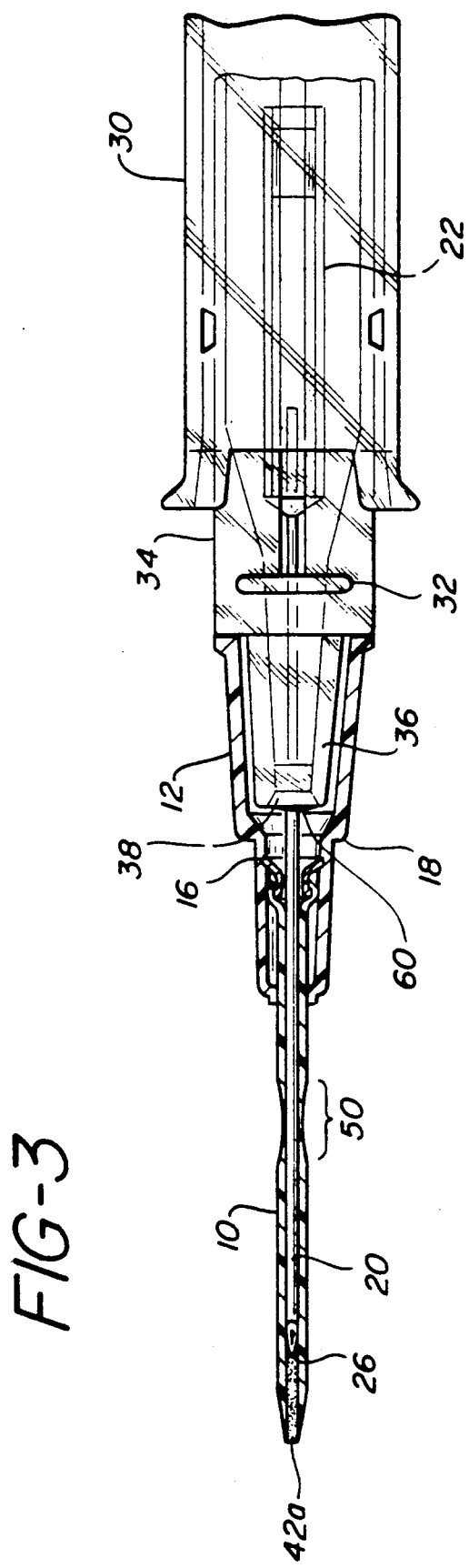

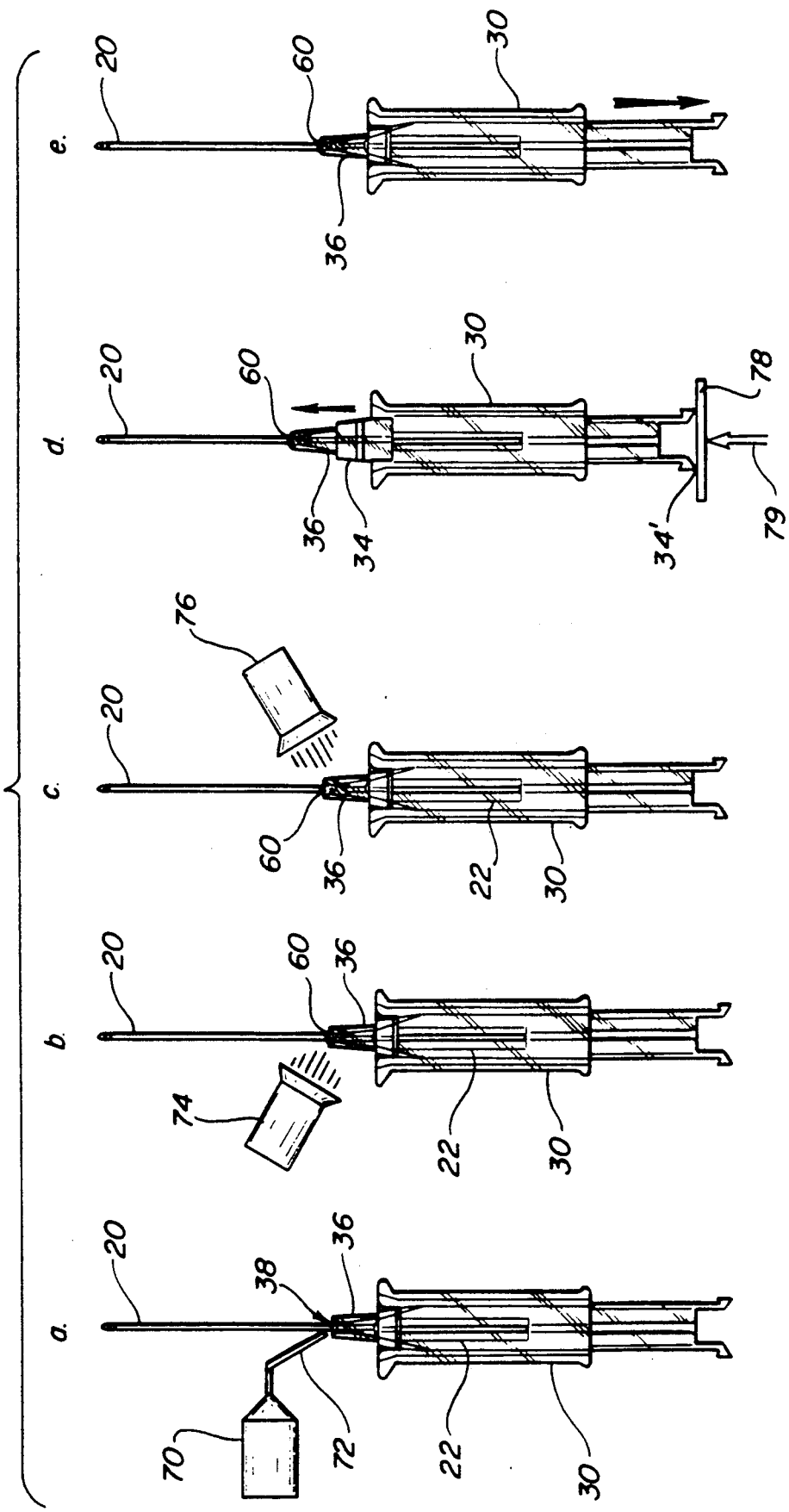

CATHETER WITH NEEDLE GASKET

FIELD OF THE INVENTION

This invention relates to I.V. catheters and, in particular, to the prevention of blood backflow and blood pooling which could result in inadvertent contact with blood during the use of such catheters.

BACKGROUND OF THE INVENTION

U.S. Pat. No. 4,762,516 (Luther et al.) and U.S. patent application Ser. No. 335,472, filed Apr. 10, 1989, describe I.V. catheters with needle guards that are designed to protect medical personnel from inadvertent injury caused by needle sticks subsequent to use of the catheter needle. Such inadvertent needle sticks can result in infection by diseases borne by the blood of the patient from whose vascular system the needle has been previously withdrawn. The catheters described in this patent and patent application prevent inadvertent needle sticks by covering the needle tip with a needle guard extending from the needle hub as the needle is withdrawn from the patient's body.

It is not only desirable to protect medical personnel from the hazards of inadvertent needle sticks, but it is further desirable to provide protection from any contact with a patient's blood. Even in the use of one of the aforementioned catheters with needle guards, it is possible for medical personnel to come into contact with a patient's blood due to undesired leakage of blood from the catheter. During insertion of the needle into the vascular system of the patient, the clinician administering the catheter will try to locate the tip of the needle in a vein or artery of the patient. When the needle tip is properly located, there will be a small flow or flash of blood through the hollow needle and into the flash chamber at the proximal end of the needle. The clinician will note this presence of blood in the flash chamber as an indication of proper needle placement. The clinician can then advance the catheter into the vascular system and withdraw the needle from the patient, leaving the catheter cannula in place in the blood vessel.

As the needle tip moves to a location proximal the distal end of the catheter, blood will flow under venous or arterial pressure into the catheter and into the hollow needle. However blood may also enter the annular space between the outer wall of the needle and the inner wall of the catheter cannula. The flow of blood in this space toward the catheter hub is herein referred to as backflow. Normally, backflow of blood is of little concern, because the catheter hub is usually quickly connected to a tubing set once the needle is withdrawn from the catheter. However, in the aforementioned catheters with needle guards, the distal nose of the needle guard occupies the catheter hub prior to complete withdrawal of the needle. As the needle guard is extended along the length of the needle toward the needle tip, its extension will carry the catheter hub to simultaneously thread the catheter into the vein or artery of the patient. The termination of this motion will eject the catheter hub from the nose of the guard when the guard reaches it full extention. Thus, if blood backflow into the catheter hub occurs prior to ejection of the catheter hub from the nose of the guard, the needle guard will be contaminated with the patient's blood prior to the release of the catheter hub. It would be desirable to prevent this contamination so that contact by medical personnel with blood on the nose of the needle guard will be prevented.

One technique for deterring blood backflow into the catheter hub is described in U.S. patent application Ser. No. 353,276, filed May 17, 1989. This technique involves the formation of a restriction by the narrowing of the inner diameter of a proximal portion of the catheter tube. The restriction causes that portion of the catheter tube to fit closely around the insertion needle, substantially deterring the flow of blood through the restriction about the needle. Only a very small amount of blood is able to pass through the restriction and flow into the catheter hub prior to withdrawal of the needle from the catheter tube.

However, once the needle is withdrawn to a position proximal the restriction, there is no impediment to blood flowing into the catheter hub and around the nose of the needle guard located inside the hub. Even though this condition is only a momentary one before the needle guard is removed from the catheter hub and the hub is connected to a tubing set, it remains desirable to deter any blood backflow both prior to and at this time. This is because blood flowing into the catheter hub may still pass through the aperture of the needle guard nose through which the needle extends. Blood backflow through the aperture of the needle guard can exit the rear of the needle guard and coat the needle, where it can inadvertently come into contact with the clinician who is inserting the catheter and removing the needle assembly. Hence, it remains desirable to prevent blood backflow through the aperture at the nose of the needle guard through which the needle passes.

SUMMARY OF THE INVENTION

In accordance with the principles of the present invention, a catheter is provided which deters the backflow of blood through the aperture at the distal end of a catheter needle guard or hub. The deterrence is provided by forming a gasket in the aperture with the needle located in the aperture, such gasket being referred to herein as a formed-in-place gasket. The gasket is formed of a material that, after has curing, will bond strongly to the needle guard or hub but not to the needle itself. The needle will thus be able to slide smoothly through the gasket and the gasket will prevent blood backflow into the needle guard or hub and will also wipe blood from the outside of the needle as it passes through the gasket.

DETAILED DESCRIPTION OF THE DRAWINGS

In the drawings:

FIG. 3 illustrates a catheter and needle assembly with a formed-in-place gasket constructed in accordance with the principles of the present invention;

FIGS. 6a-6e illustrate a process for forming the formed-in-place gasket in accordance with the principles of the present invention.

DETAILED DESCRIPTION OF THE INVENTION

Figure 1:
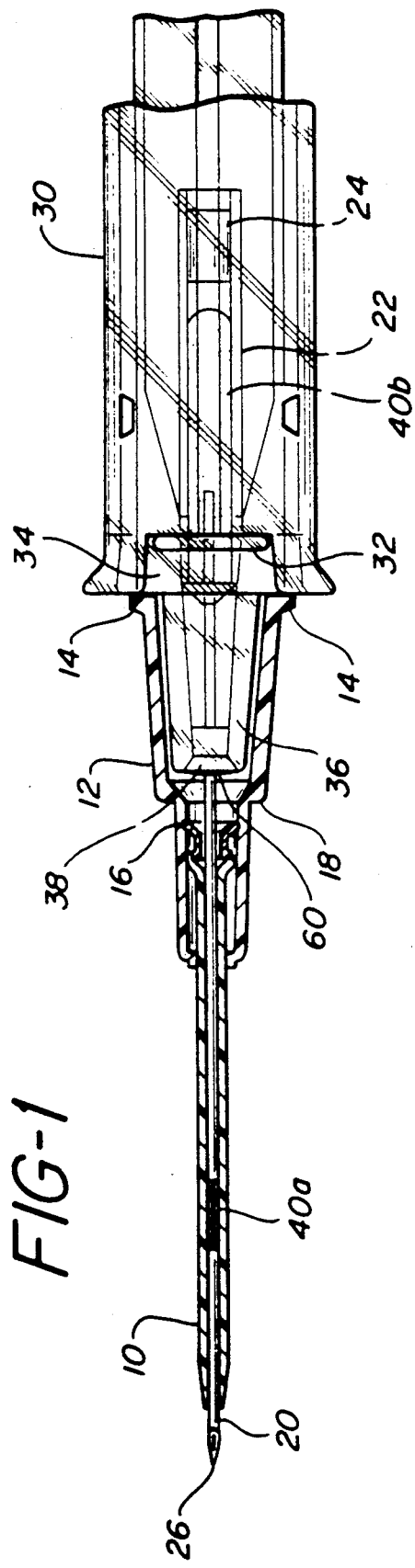
FIG. 1 illustrates a catheter and needle assembly with blood flow to the flash chamber in the needle hub.

Referring first to FIG. 1, a catheter and needle with a needle guard is shown, which may be constructed as described in the aforementioned patent and patent application Ser. No. 335,472. The assembly includes a catheter tube or cannula 10 which is connected to a catheter hub 12. A luer lock 14 is formed at the proximal end of the catheter hub 12. The cannula is attached to the hub 12 by the press fit of a flared metal sleeve 16 inside the proximal end of the cannula inside the hub 12, as described in U.S. Pat. No. 4,191,185 (Lemieux).

A hollow metal insertion needle 20 has a pointed distal end 26. The proximal end of the needle 20 is adhesively attached to the distal end opening of a flash chamber 22, which is mounted inside a needle hub or housing 30. The mounting of the flash chamber to the housing is not visible in the drawing, and comprises a longitudinal, rail-like extension from the interior of the housing to the outside of the flash chamber. The proximal end of the flash chamber is plugged by a porous plug 24 as described in U.S. patent application Ser. No. 221,579, filed July 20, 1988. The porous plug vents air from the flash chamber as the chamber fills with blood, and the pores of the plug are of insufficient size to permit blood to pass therethrough.

Slideably mounted inside the needle housing 30 is a needle guard 34, shown in its retracted position in FIG. 1. The interior of the needle guard is hollow to accommodate the flash chamber therein. The needle guard has a longitudinal opening or slot in one side through which the mounting extension of the flash chamber passes. The distal end or nose 36 of the needle guard is tapered and contains a distal aperture 38 for passage of the needle through the guard as the guard is extended. The catheter hub 12 mounts on the nose 36 of the needle guard and travels on the nose as the guard is extended until the catheter and hub are ejected when the guard is fully extended over the needle.

FIG. 1 also shows the desired flow of blood into the catheter assembly when the needle tip is properly located in a blood vessel. Blood will flow under arterial or venous pressure through the hollow needle as shown at 40a and into the flash chamber 22 as shown at 40b.

Figure 2:
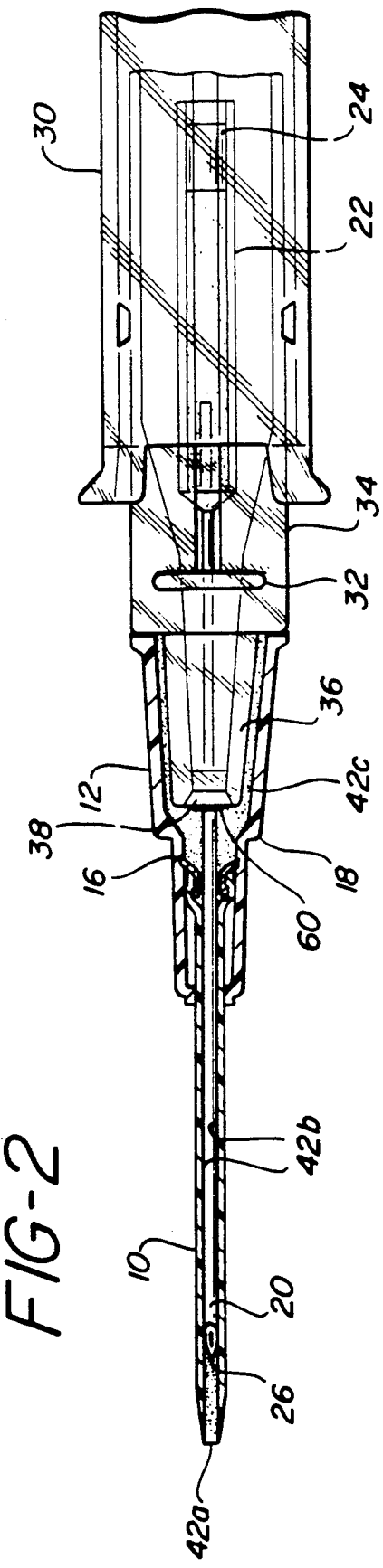
FIG. 2 illustrates the problem of blood backflow and blood pooling at the nose of the needle guard.

FIG. 2 shows the relative position of the components of the catheter assembly after the needle tip has been located in a blood vessel. At this time the needle guard 34 is extended by the clinician by pressing the guard's push-off tab 32 in the distal direction. This motion causes the needle tip 26 to retract relative to the distal end of the catheter 10 to the position shown in FIG. 2, which is referred to as "hooding" of the needle tip inside the distal end of the catheter. When the needle tip 26 is hooded, blood flows into and fills the distal end of the catheter as indicated at 42a. But in addition to the desired flow of blood through the hollow needle as shown in FIG. 1, blood may also flow into and through the small annular space between the outside of the needle and the inside of the catheter cannula, as indicated at 42b. This backflow of blood can reach the interior of the catheter hub 12 where blood pooling will occur, as indicated at 42c. This pooling of blood will undesirably contaminate the outside of the needle guard nose 36, and can also flow into the nose of the needle guard through the aperture 38 as indicated at 42d. It is an object of the present invention to prevent this backflow of blood into the nose of the needle guard.

FIG. 3 shows a catheter constructed in accordance with the principles of the present invention. This catheter assembly includes a restriction 50 formed in the catheter cannula 10 in the vicinity of the catheter hub 12, which is the subject of the aforementioned U.S. patent application Ser. No. 353,276. The restriction 50 comprises a reduction of the inside diameter of the catheter cannula to a size that closely fits around the outer diameter of the needle 20. As FIG. 3 shows, blood will still flow into the distal end of the catheter cannula 10 and around the hooded tip 26 of the needle, and may even begin to backflow through the annular space between the needle and the cannula. But when the backflow of blood reaches the restriction 50 the relatively tight fit of the cannula and the needle deters further blood backflow into the catheter hub. This substantially prevents contamination of the needle guard nose by blood pooling around the nose 36 of the needle guard inside the catheter hub.

In accordance with the principles of the present invention, any blood backflow which passes through the restriction 50 and into the catheter hub 12 is deterred from entering the nose 36 of the needle guard 34 by the presence of a gasket 60 in the aperture 38 around the needle. Blood is prevented from entering the needle guard where it can leak out and come into contact with a clinician, and the withdrawal of the needle in the proximal direction through the gasket 60 will cause the gasket to wipe the blood from the outside of the needle 20.

Figure 4A:
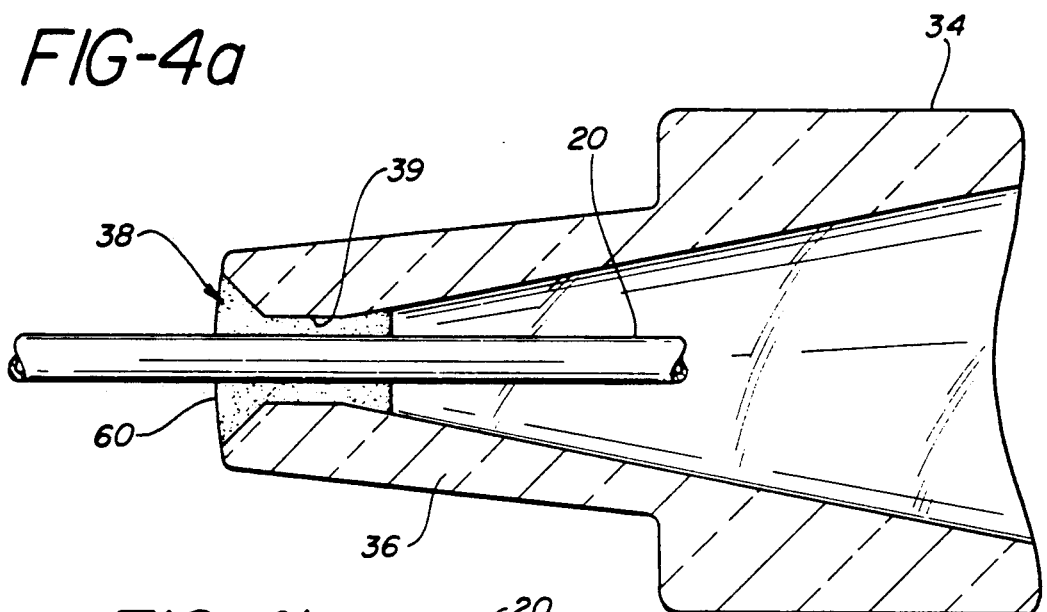
FIGS. 4a, 4b, 5a and 5b are detailed end and cross sectional views of the formed-in-place gasket.
Figure 4B:
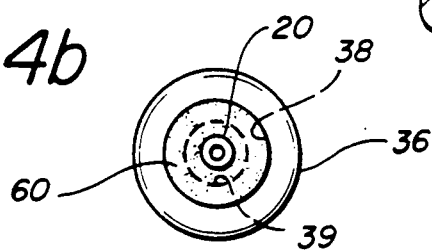

The desirability of a formed-in-place gasket rather than use of a preformed gasket such as an O-ring, Teflon ring gasket, or the like is illustrated with reference to FIGS. 4a, 4b, 5a, and 5b. FIG. 4a shows the gasket 60 formed in the aperture 38 at the distal end of the needle guard nose 36. The needle 20 is substantially concentric with the aperture 38, and particularly the narrow diameter portion 39 of the aperture. The concentric alignment of the components is illustrated in the end view of the needle guard nose of FIG. 4b.

Figure 5A:
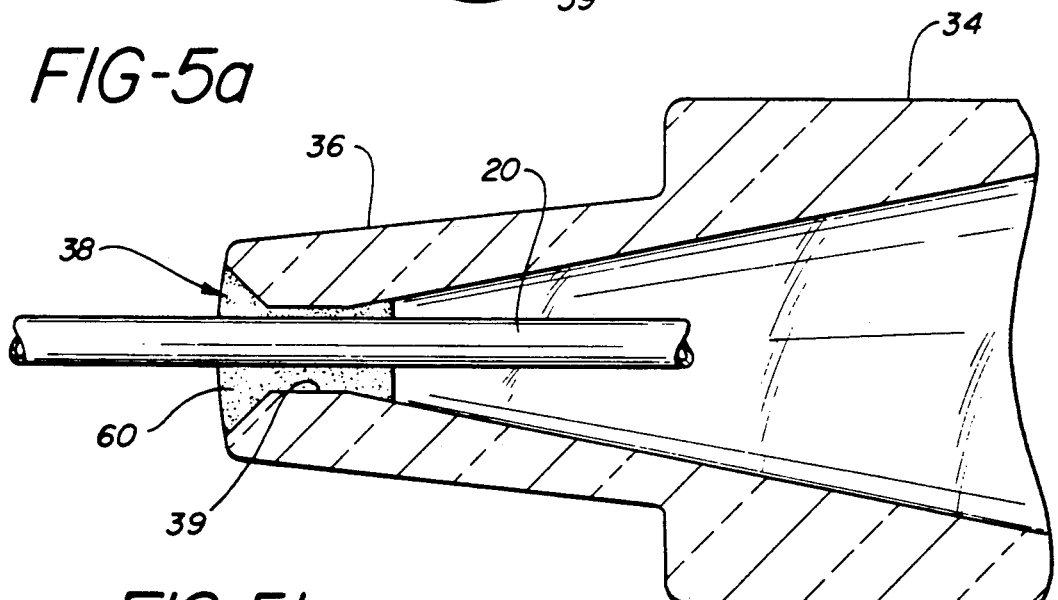
Figure 5B:
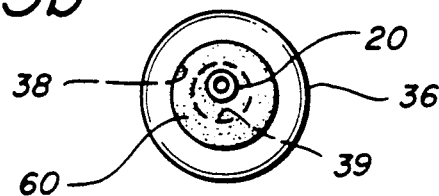

However, due to the need to assure that the needle guard nose will slide freely along the needle, the tolerances of the component and aperture alignment is intentionally relaxed. Thus, the needle may not always be concentrically aligned with the aperture 38, 39. This condition is illustrated in FIG. 5a, which shows the needle 20 passing through the aperture 38, 39 near the top of the aperture. This eccentric alignment is clearly shown in the end view of the needle guard nose of FIG. 5b. By using a flowing material to form the gasket, the gasket will form about the needle in whatever the alignment of the needle may be with respect to the aperture 38, 39. The formed-in-place gasket thereby assures the integrity of the gasket while allowing the needle guard to slide smoothly along the needle regardless of the eccentricity of the alignment of the components of the catheter assembly.

FIGS. 6a–6e illustrate a preferred technique for forming the formed-in-place gasket 60 of the present invention. In these drawings an adhesive which is cured by ultraviolet (UV) light is used to form the gasket. One suitable adhesive is type LV 3021-69 adhesive, available from the Amicon Company. Other suitable UV curing compounds are available from the Loctite and Dymax companies. The UV adhesive is desirable for its ability to cure rapidly in a high volume manufacturing process, and its ability to form a 100% solid gasket. Prior to formation of the gasket the needle 20, the needle housing 30, the needle guard 34, and the needle 20 are assembled with the needle adhesively attached to the distal end opening of the flash chamber 22 and the needle guard 34 mounted within the housing 30 to slide along the needle. The needle 20 is lubricated with a lubricant such as 0.1% Dow Corning silicone in a hexane solvent. The lubricant may be applied to the needle by spraying or dipping the needle in the lubricant.

The adhesive is applied to the aperture 38 about the needle 20 as shown in FIG. 6a by a dispenser 70 such as an EFD model XL-100 adhesive dispenser. In a preferred embodiment the adhesive is applied by a cannula 72 with a 24 gauge needle tip. About 0.5 to 3 milligrams of adhesive is applied to the needle guard aperture under a pressure of about 18 p.s.i. for approximately 0.8 seconds. With the needle assembly held in the vertical position as shown in the drawing the adhesive will fill the aperture about the needle. The needle assembly then moves to the second station, shown in FIG. 6b, where the adhesive is cured for 0.5 to 1.0 seconds by light from a UV light source 74. A suitable UV light source is commercially available from the Dymax Company. The needle assembly then moves to the third station, shown in FIG. 6c, where the adhesive is illuminated by a second UV light source 76, which uniformly cures the adhesive. The needle assembly is illuminated at the third station for an additional 0.5 to 1.0 seconds to complete the UV illumination process.

Immediately after UV illumination the needle assembly is moved to the fourth station shown in FIG. 6d. Within one second of completion of illumination at the third station the adhesive has cured sufficiently to bond securely to the plastic needle guard nose, but has not yet formed a secure bond with the lubricated metallic needle 20. Before the adhesive can bond tightly to the needle, the needle guard 34 is pushed up around the needle by a platform 78 which is urged against the proximal end 34' of the needle guard, as indicated by the arrow 79. With the needle housing 30 securely held, the upward force of the platform 78 will break any bonding of the adhesive to the needle and the needle guard 34 with its nose 36 will slide a small distance upward toward the distal end of the needle as shown in FIG. 6d. The upward force is then removed and the needle guard is allowed to slide or is mechanically slid back downward as shown in FIG. 6e. The needle assembly is then finished and the needle guard and gasket will thereafter slide smoothly along the needle. The catheter and catheter hub may then be assembled over the needle and nose 36 of the needle guard to finish the catheter assembly.

Other adhesives may be used to form the gasket 60. A hot melt adhesive such a paraffin or a polyester or polyamide type material, available from the H. B. Fuller company, may also be employed. A hot melt adhesive also desirably forms a 100% solid gasket which will cool and cure quickly due to its small thermal mass. Again the needle guard is exercised to slide the needle guard and gasket along the needle before the hot melt adhesive can bond tightly to the needle. A soluble adhesive material may also be used such as a 30% TPH, PVC or polyurethane material in a hexane and propanol solvent carrier. A greater volume of the soluble adhesive (e.g., 3-5 mg.) must be used because a gasket formed of these materials will shrink as the solvent evaporates. Tests with these materials have shown that the evaporation process can result in the creation of voids in the cured gasket. Silicone rubber is also a suitable gasket material but poses the problem of extended curing times which will impede a high speed manufacturing operation.

In conclusion, an acceptable formed-in-place gasket can be formed using any of the above materials. Such a gasket will prevent the backflow of blood into the needle guard through the aperture surrounding the needle, and the gasket will wipe blood from the outer surface of the needle as the needle guard is extended to shield the needle. The removed needle assembly with the shielded needle can then be safely handled with a substantial reduction in the instances of clinician contact with the patient's blood.

What is claimed is:

1. A catheter assembly comprising a catheter and a hollow needle insertable into said catheter, said hollow needle having a pointed distal tip, a needle housing, and a flash chamber attached to the proximal end of said needle, said needle housing upon which is emplaced said catheter, having a distal aperture through which said needle extends, and a gasket formed in said aperture about said needle to retard the flow of blood through said aperture and into said housing, wherein said needle housing further includes an integral needle guard mounted to slide along said needle, and wherein said aperture is located at the distal end of said needle guard, and wherein said gasket is made from a cured adhesive material, and said adhesive material is cured within said aperture.

2. The catheter assembly of claim 1, wherein said gasket is formed of an adhesive which is cured by ultraviolet light.

3. The catheter assembly of claim 1, wherein said gasket is formed of a hot melt adhesive.

4. The catheter assembly of claim 1, wherein said gasket is formed of an adhesive with a solvent carrier.

5. A catheter assembly comprising: a catheter containing a catheter hub, and a hollow needle insertable into said catheter, said hollow needle having a pointed distal tip and a flash chamber attached to the proximal end of said needle;

a needle housing containing an integral slidable needle guard located distal said flash chamber and having a distal nose piece for engaging said catheter hub, with an aperture through which said needle passes when said guard slides relative to said needle to shield the distal tip of said needle; and a gasket located in said aperture to prevent the flow of blood into said needle guard through said aperture, said gasket made from a cured adhesive material.

6. The catheter assembly of claim 5, wherein said gasket is formed in said aperture when said needle is located within said aperture.

7. The catheter assembly of claim 6, wherein said gasket is formed of one of an adhesive which is cured by ultraviolet light, a hot melt adhesive, or a solvent based adhesive.

8. The catheter assembly of claim 7, wherein said adhesive is bonded to said needle guard but is not bonded to said needle.

* * * * *